(12) United States Patent
Claiborne et al.

(10) Patent No.: US 6,376,530 B1
(45) Date of Patent: Apr. 23, 2002

(54) CYCLIC AMIDINES USEFUL AS NMDA NR2B ANTAGONISTS

(75) Inventors: Christopher F. Claiborne, Lansdale; Nigel J. Liverton, Harleysville; David A. Claremon, Maple Glen, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/550,972

(22) Filed: Apr. 17, 2000

Related U.S. Application Data

(60) Provisional application No. 60/133,346, filed on May 10, 1999.

(51) Int. Cl.[7] ................... C07D 209/44; C07D 409/00; A61K 31/40
(52) U.S. Cl. .................. 514/416; 548/454; 548/471
(58) Field of Search ........................... 548/471; 514/416

(56) References Cited

U.S. PATENT DOCUMENTS 4,379,157 A    4/1983   van Hes et al. ............ 424/270

FOREIGN PATENT DOCUMENTS

| GB | 1204949 | 9/1970 |
| NL | 6610677 | 1/1967 |
| NL | 6616531 | 5/1967 |

OTHER PUBLICATIONS

Database printout 1984:610920 CAPLUS, Babichev et al., Ukr. Khim. Zh., 50(6):623–626, Jan. 1984.*
Database printout 1985: 220686 CAPLUS, Kovtunenko et al., Ukr. Khim. Zh. 50(5) 530–4, Jan. 1984.*
Database Printout 1984:610920 HCAPLUS, F. S. Babichev et al., Ukr. Khim. Zh., 50(6):623–626(1984).
Database Printout 1985:220686 HCAPLUS, V.A. Kovtunenko et al., Ukr. Khim,Zh., 50(5):530–534(1984).
Database Printout 1979:120792 HCAPLUS, D. Balode et al., Khim. Geterotsikl. Soedin., 12:1632–1635(1978.
Database Printout 1970:530924 HCAPLUS, H. Boeshagen et al., Chem. Ber., 103:3166–3181(1970.
Database Printout 1970:530992 HCAPLUS, H. Boshagen et al., GB 1204949.
Database Printout 1969:430394 HCAPLUS, W. Geiger et al., Chem. Ber., 102:961–1975(196.
Database Printout 1968:60518 HCAPLUS, NL 6616531.
Database Printout 1968:59572 HCAPLUS, NL 6610677.

* cited by examiner

*Primary Examiner*—Richard L. Raymond
*Assistant Examiner*—Hong Liu
(74) *Attorney, Agent, or Firm*—Shu Mak Lee; David L. Rose

(57) ABSTRACT

The invention encompasses novel compounds of Formula I as well as a method of treating NMDA mediated diseases comprising administration to a patient in need of such treatment a non-toxic amount of a compound of Formula I effective to block the NMDA NR2B receptor sub-unit.

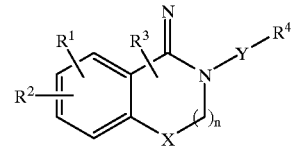

I

The invention also encompasses certain pharmaceutical compositions for the treatment of NMDA mediated diseases comprising compounds of Formula I and a pharmaceutically acceptable carrier.

17 Claims, No Drawings

CYCLIC AMIDINES USEFUL AS NMDA NR2B ANTAGONISTS

This application claims the benefits of U.S. Provisional Application No. 60/133,346, filed May 10, 1999.

BACKGROUND OF THE INVENTION

The invention relates to novel compounds and method of treating NMDA mediated diseases comprising administration to a patient in need of such treatment a non-toxic amount of these compounds effective to block the NMDA NR2B receptor sub-unit. In particluar, this invention relates to cyclic amidines useful as NMDA NR2B antagonists. The compounds of the instant invention are useful for the relief of neurological and neurodegenerative diseases, including pain, (and in particular neuropathic pain), epilepsy, stroke, anxiety, cerebral ischemia, muscular spasms, Alzheimer's Disease, Huntington's Disease and Parkinson's Disease.

The analgesic effects of NMDA receptor antagonists in man is well established. However, ion channel antagonists such as ketamine and dextromethorphan produce hallucinations, sedation, and ataxia at doses only marginally higher than the analgesic dose. The NR2B receptor is found presynaptically on most small sensory fibres entering the spinal dorsal horn as well as postsynaptically unlike other NMDA receptors which are exclusively postsynaptic. This restricted distribution lowers the probability of side effects and makes the target highly attractive for the treatment of neuropathic and other pain conditions.

NMDA Receptor Background

Glutamate plays a key role in processes related to chronic pain and pain-associated neurotoxicity, largely acting through N-methyl-D-aspartate (NMDA) receptors. Much evidence points to the involvement of NMDA receptors in the development and maintenance of neuropathic pain. NMDA receptor antagonists, for example ketamine, dextromethorphan and CPP (3-(2-carboxypiperazin-4-yl)-propyl-1-phosphonic acid) have been reported to produce symptomatic relief in a number of neuropathies including postherpetic neuralgia, central pain caused by spinal cord injury and phantom limb pain (Kristensen et al., 1992; Eide et al., 1995; Knox et al., 1995; Max et al., 1995). However, at analgesic doses psychotomimetic effects that include dizziness, headache, hallucinations, dysphoria and disturbances of cognitive and motor function prohibit their widespread use. In order to exploit NMDA receptor antagonists as possible treatment of neuropathic pain it is necessary to develop new agents with a reduced side-effect profile.

Native NMDA receptors are heterodimers composed of an NMDA R1 (NR1) subunit and at least one NMDA R2 (NR2) subunit. Receptor cloning strategies have identified multiple NMDA receptor subunits in the CNS including the NR1 subfamily (with eight isoforms derived from alternative splicing of a single gene) and four NR2 subunits (A, B, C, and D) each encoded by a single gene (for review, see Whiting & Priestly, 1996). Functional receptors have different physiological and pharmacological properties and are differentially distributed in the mammalian CNS, demonstrating the functional heterogeneity of NMDA receptors (Ishii et al., 1993; Wenzel et al., 1995; Laurie et al., 1997).

NR1 is found throughout the brain whereas NR2 subunits show a differential distribution. In particular whereas NR2C is heavily expressed and NR2A is moderately expressed in the cerebellum, there is negligible expression of NR2B in this structure. Immunocytochemical studies have demonstrated a restricted distribution of the NR2B subunit, with moderate labeling of fibres in laminas I and II of the dorsal horn suggesting a presynaptic location on primary afferent fibres and possible involvement in pain transmission (Boyce et al., 1999). The patterns of staining observed in the spinal cord, together with the data showing negligible expression of NR2B in the cerebellum, suggest that NR2B antagonists may possess antinociceptive effects, but with a reduced side effect profile than non-competitive NMDA antagonists or glycine site antagonists.

The NR2B selective antagonist CP-101,606 has been reported to possess antinociceptive activity in animal assays of inflammatory hyperalgesia (Taniguchi et al., 1997; Sakurada et al, 1998). In an animal assay of inflammatory hyperalgesia (carrageenan-induced mechanical hyperalgesia) NR2B antagonists CP-101,606 and Ro 25-6981 possess antinociceptive activity with a significant separation between analgesic doses and those which induced motor impairment (Boyce et al., 1999). NR2B antagonists are active in a wide range of animal nociceptive assays, suggesting a clinical utility for other painful conditions in addition to those caused by nerve damage. Moreover these compounds may have a reduced propensity to elicit ataxic effects of ketamine and other NMDA ion channel antagonists.

There is a wealth of in vitro and animal model data which suggests that changes in the glutamatergic system (receptors, uptake, release) increase neuronal sensitivity to previous physiological stimuli and thereby trigger secondary neuronal damage. The primary pathology underlying the generation of symptoms in Parkinson's disease is degeneration of dopaminergic neurons of the nigrostriatal pathway (Hornykiewcz, 1966). Subsequent to loss of striatal dopamine, a series of changes in activity of the basal ganglia circuitry arise, including increased activity in striatal outputs to the lateral segment of the globus pallidus. Overactivity of the striatolateral pallidal pathway is thought to be responsible for the generation of parkinsonian symptoms. It has been demonstrated that selective blockade of NR2B-containing NMDA receptors with the polyamine antagonists ifenprodil and eliprodil cause a significant increase in locomoter activity in a rodent model (Nash et al., 1999) and ifenprodil has demonstrated activity in a primate model of Parkinson's disease (Mitchell et al., 1995).

LITERATURE

Boyce, S., Chan, C.-C., Gordon, R., Li, C.-S., Rodger, I. W., Webb, J. K., Rupniak, N. M. J., Hill, R. G., 1994. L-745,337: a selective inhibitor of cyclooxygenase-2 elicits antinociception but not gastric ulceration in rats. Neuropharmacology 33, 1609–1611.

Boyce, S., Wyatt, A., Webb, J. K., O'Donnell, R., Mason, G., Rigby, M., Sirinathsinghji, D., Hill, R. G., & Rupniak, N. M. J. 1999. Selective NMDA NR2B antagonists induce antinociception without motor dysfunction: correlation with restricted localisation of NR2B subunit in dorsal horn. Neuropharmacology 38: 611–623.

Eide, K., Stubhaug, H., Oye, I., Breivik, H., 1995. Continuous subcutaneous administration of the N-methyl-D-aspartate (NMDA) receptor antagonist ketamine in the treatment of postherpetic neuralgia. Pain 61: 221–228.

Grimwood, S., Gilbert, E., Ragan, C. I., Hutson, P. H., 1996a. Modulation of 45 Ca 2++ influx into cells stably expressing recombinant human NMDA receptors by ligands acting at distinct recognition sites. J. Neurochem. 66, 2589–2595.

Grimwood, S., Le Bourdelles, B., Atack, J. R., Barton, C., Cockett, W., Cook, S. M., Gilbert, E., Hutson, P. H., McKernan, R. M., Myers, J., Ragan, C. I., Wingrove, P.

B., & Whiting, P. J. 1996b. Generation and characterisation of stable cell lines expressing recombinant human N-methyl-D-aspartate receptor subtypes. Journal of Neurochemistry 66:2239–2247.

Hornykiewcz, O. 1966. Dopamine and brain function. Pharmacol. Rev. 18:925–964.

Ishii, T., Moriyoshi, K., Sugihara, H., Sakurada, K., Kadotani, H., Yokoi, M., Akazawa, C., Shigemoto, R., Mizuno, N., Masu, M. et al., 1993. Molecular characterization of the family of the N-methyl-D-aspartate receptor subunits. J. Biol. Chem., 268, 2836–2843.

Knox, D. J., McLeod, B. J., Goucke, C. R., 1995. Acute phantom limb pain controlled by ketamine. Anaesth. Intensive Care 23, 620–622.

Kristensen, J. D., Svensson, B., Gordh Jr., T., 1992. The NMDA-receptor antagonist CPP abolishes neurogenic 'wind-up pain' after intrathecal administration in humans. Pain, 51, 249–253.

Laurie, D. J., Bartke, I., Schoepfer, R., Naujoks, K., Seeburg, P. H., 1997. Regional, developmental and interspecies expression of the four NMDAR2 subunits, examined using monoclonal antibodies. Brain Res. Mol. Brain Res. 51, 23–32.

Max, M. B., Byas-Smith, M. G., Gracely, R. H., Bennett, G. J., 1995. Intravenous infusion of the NMDA antagonist, ketamine, in chronic posttraumatic pain with allodynia: a double-blind comparison to alfentanil and placebo. Clin. Neuropharmacol. 18, 360–368.

Mitchell, I J, Hughes, N., Carroll, C B, Brotchie, J M. 1995. Reversal of parkinsonian symptoms by intrastriatal and systemic amnipulations of excitatory amino acid and dopamine transmission in the bilateral 6-OHDA lesioned marmoset. Behav. Pharmacol. 6, 492–507.

Nash, J E, Hill, M P & Brotchie, J M. 1999. Antiparkinsonian Actions of blockade of NR2B-containing NMDA receptors in the Reserpine-treated Rat. Experimental Neurology 155,42–48.

Sakurada, T., Wako, K., Sugiyama, A., Sakurada, C., Tan-Ko, K., Kisara, K., 1998. Involvement of spinal NMDA receptors in capsaicin-induced nociception. Pharmacol. Biochem. Behav. 59, 339–345.

Taniguchi, K., Shinjo, K., Mizutani, M., Shimada, K., Ishikawa, T., Menniti, F. S., Nagahisa, A., 1997. Antinociceptive activity of CP-101,606, an NMDA receptor NR2B subunit antagonist. Br. J. Pharmacol. 122, 809–812.

Wenzel, A., Scheurer, L., Kunzi, R., Fritschy, J.-M., Mohler, H., Benke, D., 1995. Distribution of NMDA receptor subunit proteins NR2A, 2B, 2C, and 2D in rat brain. NeuroReport 7, 45–48.

Whiting, P J & Priestly, T. 1996. The molecular biology of NMDA type glutamate receptors. In: Turner, A J, Stephenson, F A (eds) Frontiers of Neurobiology 3, Amino Acid Neurotransmission. Portland Press, London, 153–176.

SUMMARY OF THE INVENTION

The invention encompasses novel compounds of Formula I as well as a method of treating NMDA mediated diseases comprising administration to a patient in need of such treatment a non-toxic amount of a compound of Formula I effective to block the NMDA NR2B receptor sub-unit.

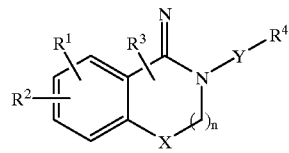

The invention also encompasses certain pharmaceutical compositions for the treatment of NMDA mediated diseases comprising compounds of Formula I and a pharmaceutically acceptable carrier.

DETAILED DESCRIPTION OF THE INVENTION

The invention encompasses novel compounds of Formula I as well as a method of treating NMDA mediated diseases comprising administration to a patient in need of such treatment a non-toxic amount of a compound of Formula I effective to block the NMDA NR2B receptor sub-unit.

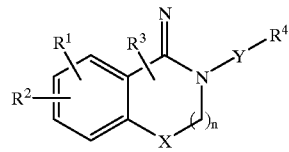

or a pharmaceutically acceptable salt thereof wherein:
  $R^1$ is selected from the group consisting of
    (a) hydrogen,
    (b) $C_{1-6}$alkyl,
    (c) Br, Cl, F or I,
    (d) $C_{1-6}$alkoxy, optionally mono or di- or tri-substituted with a halo independently selected from Br, Cl, F and I,
  $R^2$ is selected from the group consisting of
    (a) $C_{1-6}$alkyl,
    (b) Br, Cl, F or I,
    (c) $C_{1-6}$alkoxy, optionally mono or di- or tri-substituted with a halo independently selected from Br, Cl, F and I,
  or $R^1$ and $R^2$ may be joined so that together with the atoms to which they are attached there is formed a ring selected from the group consisting of
    (a) cyclopentane,
    (b) cyclohexane,
    (c) furan,
    (d) phenyl, and
    (e) a five (5) or six (6) membered saturated or unsaturated heterocycle containing one, two or three heteroatoms selected from the group consisting of S, O and N,
    said ling optionally mono, di, tri or tetra-substituted with a halo independently selected from Br, Cl, F and I;
  $R^3$ is hydrogen or $C_{1-6}$alkyl;
  $R^4$ is selected from the group consisting of
    (a) hydrogen,
    (b) phenyl or naphthyl, optionally mono, di- or tri-substituted with substituents independently selected from
      (1) $C_{1-6}$alkyl,
      (2) Br, Cl, F or I, (3) $C_{1-6}$alkoxy, optionally mono or di- or tri-substituted with a halo independently selected from Br, Cl, F and I;

n is 0, 1 or 2,

X is selected from
- (a) $CH_2$,
- (b) O
- (c) S,
- (d) S(O),
- (e) $S(O)_2$, and
- (f) N—R, wherein R is selected from
  - (1) hydrogen,
  - (2) $C_{1-6}$alkyl,
  - (3) $C_{1-6}$alkylsulfonyl,
  - (4) $C_{1-6}$alkylcarbonyl,
  - (5) $C_{1-6}$alkoxycarbonyl; and Y is $C_{1-6}$alkylene.

Within this embodiment there is a genus of compounds of Formula I wherein $R^1$ is selected from the group consisting of
- (a) hydrogen,
- (b) Br, Cl, F or I, and
- (c) $C_{1-3}$alkoxy, optionally mono or di- or tri-substituted with a halo independently selected from Br, Cl, F and I.

Within this genus there is a class of compound of Formula I wherein $R^1$ is selected from the group consisting of
- (a) hydrogen,
- (b) Br, Cl, F or I , and
- (c) $C_{1-3}$alkoxy, optionally mono or di- or tri-substituted with a halo independently selected from Br, Cl F and I; and $R^2$ is selected from the group consisting of
- (a) Br, Cl, F or I, and
- (b) $C_{1-3}$alkoxy, optionally mono or di- or tri-substituted with a halo independently selected from Br, Cl, F and I.

Within this embodiment there is second genus of compounds of Formula I wherein $R^3$ is selected from the group consisting of
- (a) hydrogen, and
- (b) $C_{1-3}$alkyl.

Within this embodiment there is a third genus of compound of Formula I wherein $R^4$ is selected from the group consisting of
- (a) hydrogen,
- (b) phenyl or naphthyl, optionally mono, di- or tri-substituted with substituents independently selected from
  - (1) $C_{1-3}$alkyl,
  - (2) Br, Cl, F or I,
  - (3) $C_{1-3}$alkoxy, optionally mono or di- or tri-substituted with a halo independently selected from Br, Cl, F and I.

Within this embodiment there is a fourth genus of compound of Formula I wherein

X is selected from
- (a) $CH_2$,
- (b) O,
- (c) S,
- (d) S(O),
- (e) S(O)2, and
- (f) N—R, wherein R is selected from
  - (1) hydrogen,
  - (2) $C_{1-3}$alkyl,
  - (3) $C_{1-3}$alkylsulfonyl,
  - (4) $C_{1-3}$alkylcarbonyl, and
  - (5) $C_{1-3}$alkoxycarbonyl.

Within this embodiment there is a fifth genus of compounds of Formula I wherein

Y is methylene or ethylene.

Within this embodiment there is a sixth genus of compounds of Formula I wherein n is 1.

Within this genus there is a class of compounds of Formula I wherein $R^1$ is selected from the group consisting of
- (a) hydrogen,
- (b) Br, Cl, F or I, and
- (c) $C_{1-3}$alkoxy, optionally mono or di- or tri-substituted with a halo independently selected from Br, Cl, F and I; and $R^2$ is selected from the group consisting of
- (a) Br, Cl, F or I, and
- (b) $C_{1-3}$alkoxy, optionally mono or di- or tri-substituted with a halo independently selected from Br, Cl, F and I;

$R^3$ is selected from the group consisting of
- (a) hydrogen, and
- (b) $C_{1-3}$alkyl;

R4 is selected from the group consisting of phenyl or naphthyl, optionally mono, di- or tri-substituted with substituents independently selected from
- (a) $C_{1-3}$ alkyl,
- (b) Br, Cl, F or I,
- (c) $C_{1-3}$alkoxy, optionally mono or di- or tri-substituted with a halo independently selected from Br, Cl, F and I, X is selected from
- (a) $CH_2$,
- (b) O,
- (c) S,
- (d) S(O),
- (e) $S(O)_2$, and
- (f) N—R, wherein R is selected from
  - (1) hydrogen,
  - (2) $C_{1-3}$alkyl,
  - (3) $C_{1-3}$alkylsulfonyl,
  - (4) $C_{1-3}$alkylcarbonyl,
  - (5) $C_{1-3}$alkoxycarbonyl; and Y is methylene or ethylene.

In a second embodiment the invention encompasses non-toxic pharmaceutical compositions comprising a therapeutically effective amount of compound of Formula I and a pharmaceutically acceptable carrier.

In a third embodiment the invention encompasses a method of treating a NMDA mediated diseases comprising administration to a patient in need of such treatment a non-toxic amount of a compound of Formula I effective to block the NMDA NR2B receptor sub-unit.

Within the third embodiment there is a genus encompassing a method of treating pain comprising administration to a patient in need of such treatment a non-toxic amount of a compound of Formula I effective to block the NMDA NR2B receptor sub-unit.

As seen above, in some aspects of the invention $R^1$ and $R^2$ may be joined so that together with the atoms to which they are attached there is formed a 5 or 6 membered saturated or unsaturated heterocycle containing one, two or three hetero atoms selected from S, O and N. For purposes of this specification these heterocycles are intended to include, but are not limited to optionally mono. di, tri, or tetra halo substituted:

(1) furanyl,
(2) diazinyl,
(3) imidazolyl,
(4) isooxazolyl,
(5) isothiazolyl,
(6) oxadiazolyl,
(7) oxazolyl,
(8) pyrazolyl,
(9) pyridyl,
(10) pyrrolyl,
(11) thiadiazolyl,
(12) thiazolyl,
(13) thienyl,
(14) triazinyl,
(15) triazolyl,
(16) morpholinyl,
(17) piperazinyl,
(18) piperidenyl,
(19) pyranyl,
(20) furazanyl,
(21) dioxanyl, and
(22) dioxolanyl.

The following additional examples illustrate the manner in which $R^1$ and $R^2$ may be joined so that together with the atoms to which they are attached to form a 5 or 6 membered saturated or unsaturated heterocycle comprising a compound of Formula I.

Within the compounds of Formula I are the novel compounds of Formula II as well as a method of treating NMDA mediated diseases comprising administration to a patient in need of such treatment a non-toxic amount of a compound of Formula II effective to block the NMDA NR2B receptor sub-unit.

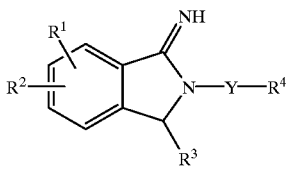

II or a pharmaceutically acceptable salt thereof wherein:

$R^1$ is selected from the group consisting of
  (a) hydrogen,
  (b) $C_{1-6}$alkyl,
  (c) Br, Cl, F or I,
  (d) $C_{1-6}$alkoxy, optionally mono or di- or tri-substituted with a halo independently selected from Br, Cl, F and I, $R^2$ is selected from the group consisting of
  (a) $C_{1-6}$alkyl,
  (b) Br, Cl, F or I,
  (c) $C_{1-6}$alkoxy, optionally mono or di- or tri-substituted with a halo independently selected from Br, Cl, F and I, or $R^1$ and $R^2$ may be joined so that together with the atoms to which they are attached there is formed a ring selected from the group consisting of:
  (a) cyclopentane,
  (b) cyclohexane,
  (c) furan,
  (d) phenyl, and
  (e) a five (5) or six (6) membered saturated or unsaturated heterocycle containing one, two or three heteroatoms selected from the group consisting of S, O and N,
  said ring optionally mono, di, tri or tetra-substituted with a halo independently selected from Br, Cl, F and I;

$R^3$ is hydrogen or $C_{1-6}$alkyl;

$R^4$ is selected from the group consisting of
  (a) hydrogen,
  (b) phenyl or naphthyl, optionally mono, di- or tri-substituted with substituents independently selected from
    (1) $C_{1-6}$alkyl,
    (2) Br, Cl, F or I,
    (3) $C_{1-6}$alkoxy, optionally mono or di- or tri-substituted with a halo independently selected from Br, Cl, F and I, and Y is $C_{1-6}$alkylene.

One a genus of compounds of Formula II are those wherein
$R^1$ is selected from the group consisting of
  (a) hydrogen,
  (b) Br, Cl, F or I, and
  (c) $C_{1-3}$alkoxy, optionally mono or di- or tri-substituted with a halo independently selected from Br, Cl, F and I.

Within this genus there is a class of compound of Formula II wherein
$R^1$ is selected from the group consisting of
  (a) hydrogen,
  (b) Br, Cl, F or I, and
  (c) $C_{1-3}$alkoxy, optionally mono or di- or tri-substituted with a halo independently selected from Br, Cl F and I; and $R^2$ is selected from the group consisting of
  (a) Br, Cl, F or I, and
  (b) $C_{1-3}$alkoxy, optionally mono or di- or tri-substituted with a halo independently selected from Br, Cl, F and I.

Within this embodiment there is second genus of compounds of Formula I wherein $R^3$ is selected from the group consisting of
  (a) hydrogen, and
  (b) $C_{1-3}$alkyl.

Within this embodiment there is a third genus of compound of Formula II wherein
$R^4$ is selected from the group consisting of
  (a) hydrogen,
  (b) phenyl or naphthyl, optionally mono, di- or tri-substituted with substituents independently selected from
    (1) $C_{1-3}$ alkyl,
    (2) Br, Cl, F of I,
    (3) $C_{1-3}$alkoxy, optionally mono or di- or tri-substituted with a halo independently selected from Br, Cl, F and I.

Within this embodiment there is a fourth genus of compounds of Formula II wherein
Y is methylene or ethylene.

Within this genus there is a class of compounds of Formula II wherein
$R^1$ is selected from the group consisting of
  (a) hydrogen,
  (b) Br, Cl, F or I, and
  (c) $C_{1-3}$alkoxy, optionally mono or di- or tri-substituted with a halo independently selected from Br, Cl, F and I; and $R^2$ is selected from the group consisting of
  (a) Br, Cl, F or I, and
  (b) $C_{1-3}$alkoxy, optionally mono or di- or tri-substituted with a halo independently selected from Br, Cl, F and I, $R^3$ is selected from the group consisting of
  (a) hydrogen, and
  (b) $C_{1-3}$alkyl;

$R^4$ is selected from the group consisting of phenyl or naphthyl, optionally mono, di- or tri-substituted with substituents independently selected from
  (a) C 1–3 alkyl,
  (b) Br, Cl, F or I,
  (c) $C_{1-3}$ alkoxy, optionally mono or di- or tri-substituted with a halo independently selected from Br, Cl, F and I; and Y is methylene or ethylene.

For purposes of this specification alkyl is defined to include linear, branched and cyclic structures, with $C_{1-6}$alkyl including methyl, ethyl, propyl, 2-propyl, s- and t-butyl, butyl, pentyl, hexyl, 1,1-dimethylethyl, cyclopropyl, cyclobutyl, cyclopentyl and cyclohexyl. Similarly, $C_{1-6}$alkoxy is intended to include alkoxy groups of from 1 to 6 carbon atoms of a straight, branched, or cyclic configuration. Examples of lower alkoxy groups include methoxy, ethoxy, propoxy, isopropoxy, cyclopropyloxy, cyclohexyloxy, and the like.

Exemplifying the invention are the examples hereunder, which include:

5-Choro-2-(2-trifluoromethoxy-benzyl)-2,3-dihydro-isoindol-1-ylideneamine Hydrobromide,
5-Chloro-2-(3,5-dimethyl-benzyl)-2,3-dihydro-isoindol-1-ylidenaeamine Hydrobromide,
5-Chloro-2-(3,5-dichloro-benzyl)-2,3-dihydro-isoindol-1-ylideneamine Hydrobromide,
5-Chloro-2-(3-methoxy-benzyl)-2,3-dihydro-isoindol-1-ylideneamine,
5,6-Dichloro-2-(3-chloro-benyl)-2,3-dihydro-isoindol-1-ylideneamine Hydrobromide,
5,6-Dichloro-2-)2-trifluoromethoxy-benzyl)-2,3-dihydro-isoindol-1-ylideneamine Hydrobromide,
5,6-Dicholoro-2-(2-methoxy-benzyl)-2,3-dihydro-isoindol-1-ylideneamine Hydrobromide,
5,6-Dichloro-2-(3-methoxy-benzyl)-2,3-dihydro-isoindol-1-ylideneamine Hydrobromide,
5,6-Dichloro-2-(3-dichloro-benzyl)-2,3-dihydro-isoindol-1-ylideneamine Hydrobromide,
5,6-Dichloro-2-(3-dimethyl-benzyl)-2,3-dihydro-isoindol-1-ylideneamine Hydrobromide,
5,6-Dichloro-2-(3-chloro-benzyl)-2,3-dihydro-isoindol-1-ylideneamine Hydrobromide,
2-(3-Chloro-benzyl)-5-trifluoromethoxy-2,3-dihydro-isoindol-1-ylideneamine Hydrobromide,
5-Trifluoromethoxy-2-(2-trifluoromethoxy-benzyl)-2,3-dihydro-isoindol-1-ylideneamine Hydrobromide,
2-(2-Methozy-benzyl)-5-trifluoromethoxy-2,3-dihydro-isoindol-1-ylideneamine Hydrobromide,
2-(3-Methozy-benzyl)-5-trifluoromethoxy-2,3-dihydro-isoindol-1-ylideneamine Hydrobromide,
2-(3,5-Dichloro-benzyl)-5-trifloromethoxy-2,3-dihydro-isoindol-1-ylideneamine Hydrobromide, and
2-(3,5-Dimethyl-benzyl)-5-trifluoromethoxy-2,3-dihydro-isoindol-1-ylideneamine Hydrobromide.

Some of the compounds described herein contain one or more asymmetric centers and may thus give rise to diastereomers and optical isomers. The present invention is meant to comprehend such possible diastereomers as well as their racemic and resolved, enantionmerically pure forms and pharmaceutically acceptable salts thereof.

Some of the compounds described herein contain olefinic double bonds, and unless specified otherwise, are meant to include both E and Z geometric isomers.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like, and basic ion exchange resins.

It will be understood that in the discussion of methods of treatment which follows, references to the compounds of Formula I are meant to also include the pharmaceutically acceptable salts.

The compound of Formula I is useful for the relief of neurological and neurodegenerative diseases, including pain, (and in particular neuropathic pain), epilepsy, stroke, anxiety, cerebral ischemia, muscular spasms, Alzheimer's Disease, Huntington's Disease and Parkinson's Disease.

For the treatment of any of these NMDA mediated diseases a compound of Formula I may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle sheep, dogs, cats, etc., the compound of the invention is effective in the treatment of humans.

As indicated above, pharmaceutical compositions for treating NMDA mediated diseases as defined may optionally include one or more ingredients as listed above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example, sodium carboxymethylcellulose, methylcellulose, hydroxy-propylmethycellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring and coloring agents, may also be present.

The pharmaceutical compositions of the invention may also be in the form of an oil-in-water emulsions. The oily phase may be a vegetable oil, for example, olive oil or arachis oil, or a mineral oil, for example, liquid paraffin or mixtures of these. Suitable emulsifying agents may be naturally-occurring phosphatides, for example, soy bean, lecithin, and esters or partial esters derived from fatty acids and hexitol anhydrides, for example, sorbitan monooleate, and condensation products of the said partial esters with ethylene oxide, for example, polyoxy-ethylene sorbitan monooleate. The emulsions may also contain sweetening and flavouring agents.

Syrups and elixirs may be formulated with sweetening agents, for example, glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example, as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, gels, solutions or suspensions, etc., containing the compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Dosage levels of the order of from about 0.01 mg to about 140 mg/kg of body weight per day are useful in the treatment of the above-indicated conditions, or alternatively about 0.5 mg to about 7 g per patient per day. For example, NMDA mediated diseases, including pain, may be effectively treated by the administration of from about 0.01 to 50 mg of the compound per kilogram of body weight per day, or alternatively about 0.5 mg to about 3.5 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 500 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

The compounds of the present invention can be prepared according to the following methods:

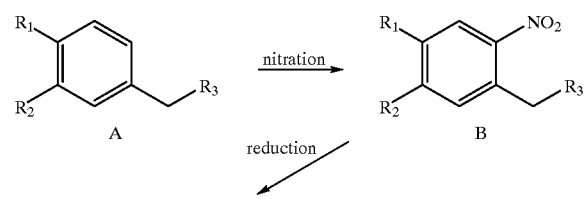

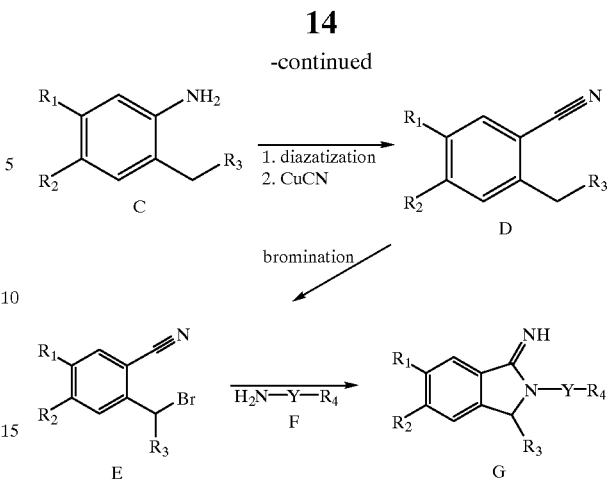

Compound A is regiospecifically nitrated to afford intermediate B. B is subjected to reducing conditions to yield the substituted aniline C which is then converted to aryl nitrile D via diazatization and treatment with copper cyanide. Compound D is bominated on the benzylic position to yield E. E is treated with a primary amine F to produce the target cyclic amidine G.

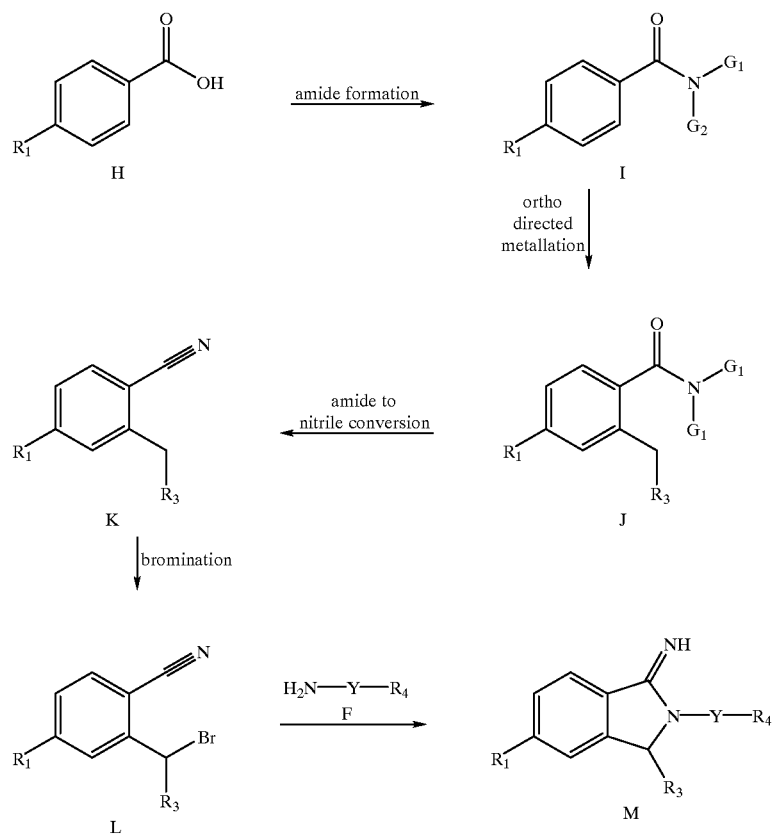

Compound H in converted to an amide, represented by I, appropiate for directing ortho metallations. Compound I is treated with base and quenched with BrCH₂—R3 to yield J. The amide in compound J is converted to the nitrile K. Bromination of K followed by treatment of L with amine F leads to the formation of cylcic amidine M.

EXAMPLE 1

(Compound 3)

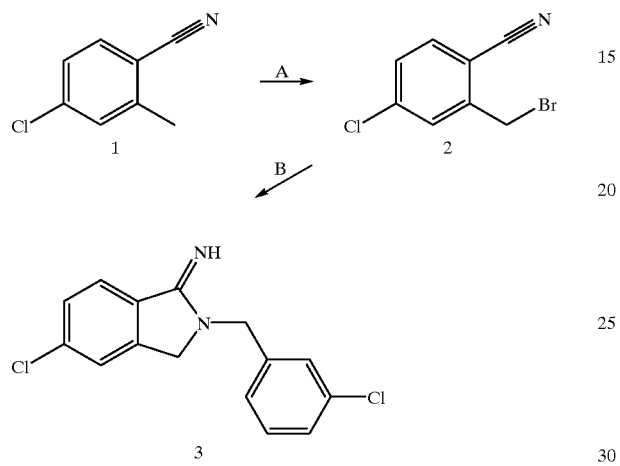

Experimental

Step A

4-Chloro-2-(bromo-methyl)-benzonitrile 2

To a stirred solution 4-Chloro-2-methyl-benzonitrile 1(5.0 g, 33.0 mmol) in carbon tetrachloride (150 mL) was added N-bromosuccinamide (7.6 g, 42.9 mmol) and 2,2'-azobisisobutyronitrile (cat.). The reaction mixture was refluxed 6 hrs, filtered, concentrated, and partitioned between ether and water. The ether layer was dried, concentrated, and purified by silica gel chromatography (10% ether/hexanes) to yield a white solid (40%). $^1$H NMR (400 MHz, CDCl$_3$) δ7.61 (d, J=8.3 Hz, 1 H, Ar), 7.57 (d, J=2.2 Hz, 1 H, Ar), 7.41 (dd, J=8.3, 2.0 Hz, 1 H, Ar), 4.59 (s, 2 H, CH$_2$).

Step B

5-Chloro-2-(3-chloro-benzyl)-2,3-dihydro-isoindol-1-ylideneamine Hydrobromide 3

To a solution of 3-chlorobenzylamine (80 mg, 0.56 mmol) in ethanol (500 mL) at 80° C. was added 4-Chloro-2-(bromo-methyl)-benzonitrile 2 (100 mg, 0.43 mmol) as a solution in ethanol (100 mL). After 30 min at 80° C., the ethanol was removed under reduced pressure, and the resulting residue was triturated with ether/ethanol to yield the title compound (colorless solid 90%). $^1$H NMR (400 MHz, DMSO-d$_6$) δ9.76 (broad s, 1 H, NH), 8.22 (d, J=8.0 Hz, 1 H, Ar), 7.85 (s, 1H, Ar), 7.78 (d, J=8.4 Hz, 1 H, Ar), 7.53 (s, 1 H, Ar), 7.45 (m, 2 H, Ar), 7.36 (m, 1 H, Ar), 5.05 (s, 2 H, CH$_2$), 4.81 (s, 2 H, CH$_2$); M/Z (ESI$^+$) 291, 293 ([M+H]$^{30}$ )

EXAMPLE 2

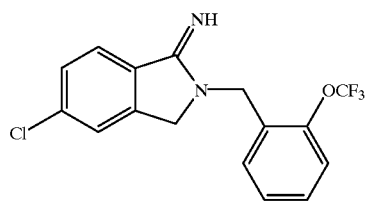

5-Chloro-2-(2-trifluoromethoxy-benzyl)-2,3-dihydro-isoindol-1-ylideneamine Hydrobromide The title compound was prepared utilizing the procedure described in Step B (Example 1) with 2-trifluoromethoxybenzylamine in place of 3-chlorobenzylamine (colorless solid>90%). $^1$H NMR (400 MHz, DMSO-d$_6$) δ8.42 (d, J=8.0 Hz, 1 H, Ar), 7.85 (s, 1 H, Ar), 7.79 (d, 1 H, J=8.0 Hz, Ar), 7.49 (m, 4 H, Ar), 5.12 (s, 2 H, CH$_2$), 4.75 (s, 2 H, CH$_2$); M/Z (ESI$^+$) 341, 343 ([M+H]$^+$).

EXAMPLE 3

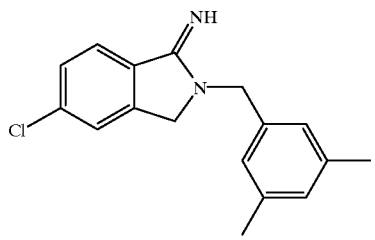

5-Chloro-2-(3,5-dimethyl-benzyl)-2,3-dihydro-isoindol-1-ylideneamine Hydrobromide The title compound was prepared utilizing the procedure described in Step B (Example 1) with 3,5-dimethylbenzylamine in place of 3-chlorobenzylamine (colorless solid 91%). $^1$H NMR (400 MHz, DMSO-d$_6$) δ9.8 (broad s, 1 H, NH), 8.23 (d, J=8.0 Hz, 1 H, Ar), 7.83 (s, 1 H, Ar), 7.78 (d, J=8.4 Hz, 1 H, Ar), 7.01 (s, 1 H, Ar), 6.99 (s, 2 H, Ar), 4.94 (s, 2 H, CH$_2$), 4.76 (s, 2 H, CH$_2$), 2.27 (s, 6 H, CH$_3$); M/Z (ESI$^+$) 285. 287 ([M+H]$^+$).

EXAMPLE 4

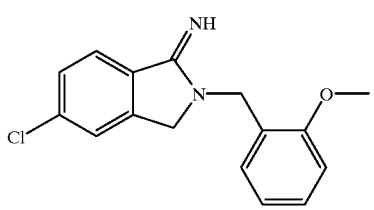

5-Chloro-2-(2-methoxy-benzyl)-2,3-dihydro-isoindol-1-ylideneamine Hydrobromide

The title compound was prepared utilizing the procedure described in Step B (Example 1) with 2-methoxybenzylamine in place of 3-chlorobenzylamine (colorless solid>90%). $^1$H NMR (400 MHz, DMSO-$d_6$) δ9.50 (broad s, 1 H, NH), 8.20 (d, J=8.4 Hz, 1 H, Ar), 7.83 (s, 1 H, Ar), 7.79 (d, J=8.4 Hz, 1 H, Ar), 7.39 (m, 1 H, Ar), 7.28 (d, J=7.6 Hz, 1 H, Ar), 7.11 (m, 1 H, Ar), 7.02 (m, 1 H, Ar), 4.95 (s, 2 H, CH$_2$), 4.72 (s, 2 H, CH$_2$), 3.83 (s, 3 H, CH$_3$); M/Z (ESI$^+$) 287, 289 ([M+H]$^+$)

lamine in place of 3-chlorobenzylamine (colorless solid 95%). $^1$H NMR (400 MHz, DMSO-$d_6$) δ8.22 (d, J=8.4 Hz, 1 H, Ar), 7.85 (s, 1 H, Ar), 7.78 (d, J=8.4 Hz, 1 H, Ar), 7.64 (s, 1 H, Ar), 7.53 (s, 2 H, Ar), 5.04 (s, 2 H, CH$_2$), 4.84 (s, 2 H, CH$_2$). M/Z (ESI$^+$) 325, 327 ([M+H]$^+$).

EXAMPLE 6

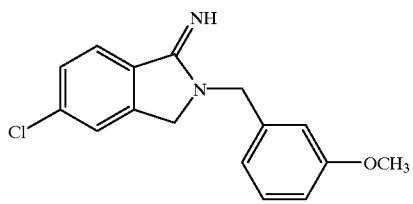

5-Chloro-2-(3-methoxy-benzyl)-2,3-dihydro-isoindol-1-ylideneamine

The title compound was prepared utilizing the procedure described in Step B (Example 1) with 3-methoxybenzylamine in place of 3-chlorobenzylamine (colorless solid>90%). $^1$H NMR (400 MHz, DMSO-$d_6$) δ9.62 (s, 1 H, NH), 8.24 (d, J=8.4 Hz, 1 H, Ar), 7.84 (s, 1 H, Ar), 7.79 (d, J=8.4 Hz, 1 H, Ar), 7.35 (m, 1 H, Ar), 6.95 (m, 3 H, Ar), 4.99 (s, 2 H, CH$_2$), 4.79 (s, 2 H, CH$_2$). 3.77 (s, 3 H, CH$_3$); M/Z (ESI$^+$) 287, 289 ([M+H]$^+$).

EXAMPLE 7

(Compound 9)

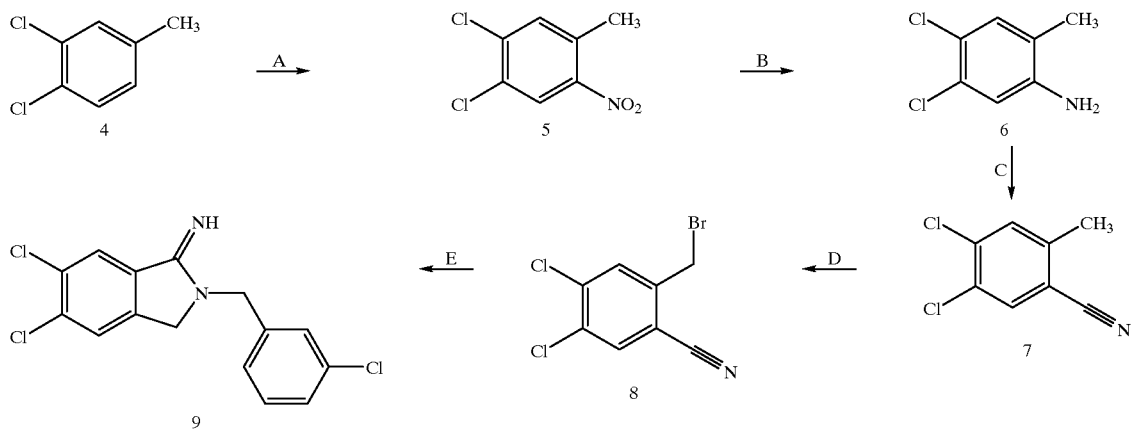

EXAMPLE 5

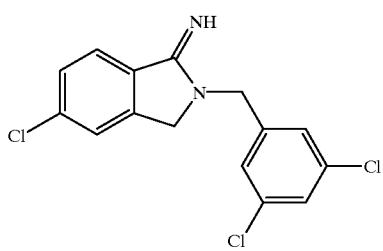

5-Chloro-2-(3,5-dichloro-benzyl)-2,3-dihydro-isoindol-1-ylideneamine Hydrobromide The title compound was prepared utilizing the procedure described in Step B (Example 1) with 3,5 dichlorobenzy- Step A 4,5-Dichloro-2-methyl-nitrobenzene 5

To stirred 3,4-dichloro-toluene 4 (10.0 g, 62.2 mmol) at 0° C. was slowly added fuming nitric acid (20.0 mL). The mixture was stirred for 2 hrs at RT, then water added (200 mL) and the reaction mixture filtered. The filtrate was purified by silica gel chromatography using 5% ethyl acetate in hexanes to give the title compound 11.7 g (92%). $^1$H NMR (400 MHz, CDCl$_3$) δ8.14 (s, 1 H, Ar), 7.47 (s , 1 H, Ar), 2.59 (s, 3 H, CH$_3$).

Step B 4,5-Dichloro-2-methyl-phenylamine 6

4,5-Dichloro-2-methyl-nitrobenzene 5 (5.0 g, 24.3 mmol) was heated at 100° C. in titanium trichloride (30% in aqueous hdyrochloric acid, 25 mL) for 2 hrs., cooled to RT, the reaction solution was basified to pH 8 with 50% aqueous sodium hydroxide, then extracted with ethyl acetate. The ethyl acetate layer was washed with water, brine, dried over sodium sulfate, filtered and concentrated. The residue was purified by silica gel chromatography using 10% ethyl acetate in hexanes to give 2.4 g (56%) of the title product. $^1$H NMR (400 MHz, CDCl$_3$) δ7.09 (s, 1 H, Ar), 6.74 (s , 1 H, Ar), 3.63 (s, 2 H, NH$_2$), 2.10 (s, 3H, CH$_3$).

Step C 4,5-Dichloro-2-methyl-benzonitrile 7

Water (250 mL) was added to a stirred mixture of 4,5-dichloro-2-methyl-phenylamine 6 (8.0 g, 45.4 mmol) in concentrated hydrochloric acid (30 mL). After cooling to 0° C., a solution of sodium nitrite (3.1 mg, 45.4 mmol) in water (10 mL) was added dropwise. After stiring for 0.5 hr, the reaction solution was brought to pH 6 with saturated aqueous sodium bicarbonate. In another flask, copper sulfate pentahydrate (13.6 g, 54.5 mmol) in water (60 mL) was added dropwise to a stirred solution of potassium cyanide (13.6 g, 209.0 mmol) in water (30 mL) at 0° C. Benzene (60 mL), was added and this second mixture heated to 60° C.

The previously prepared diazonium solution was added dropwise to the brown copper(I) cyanide solution. The resulting reaction solution was heated at 70° C. for an additional 1 hr. The reaction solution was cooled to RT, diluted with ethyl acetate, filtered through celite, dried with sodium sulfate, filtered and concentrated. The residue was crystallized from ether to give the title compound 6.3 g (75%). $^1$H NMR (400 MHz, CDCl$_3$) δ7.76 (s, 1 H, Ar), 7.44 (s, 1 H, Ar), 2.51 (s, 3 H, CH$_3$).

Step D

2-Bromomethyl-4,5-dichloro-benzonitrile 8

To a solution 4,5-Dichloro-2-methyl-benzonitrile 7 (6.3 g, 33.9 mmol) in carbon tetrachloride (50 mL) was added N-bromosuccinimide (9.0 g, 50.8 mmol) and 2,2'-azobisisobutyronitrile (cat.). The reaction mixture was refluxed 6 hrs, filtered, concentrated, and partitioned between ether and water. The ether layer was dried, concentrated, and purified by silica gel chromatography (10% ether/hexanes) to yield the tittle compound 4.0 g. (45%). $^1$H NMR (400 MHz, CDCl$_3$) δ7.75 (s, 1 H, Ar), 7.66 (s, 1 H, Ar), 2.55 (s, 2 H, CH$_3$).

Step E 5,6-Dichloro-2-(3-chloro-benzyl)-2,3-dihydro-isoindol-1-ylideneamine 9 Hydrobromide To a solution of 3-chlorobenzylamine (69 mg, 0.49 mmol) in ethanol (500 mL) at 80° C. was added 2-bromomethyl-4,5-dichloro-benzonitrile 8 (100 mg, 0.38 mmol) as a solution in ethanol (100 mL). After 30 min at 80° C., the ethanol was removed under reduced pressure, and the resulting residue triturated with ether/ethanol to yield the title compound (colorless solid>90%). $^1$H NMR (400 MHz, DMSO-d$_6$) δ9.77 (s, 1 H, NH), 8.52 (s, 1 H, Ar), 8.06 (s, 1 H, Ar), 7.52 (s, 1 H, Ar), 7.45 (m, 2 H, Ar), 7.37 (m, 1 H, Ar), 5.04 (s, 2 H, CH$_2$), 4.82 (s, 2 H, CH$_2$); M/Z (ESI$^+$) 325, 327 ([M+H]$^+$).

EXAMPLE 8

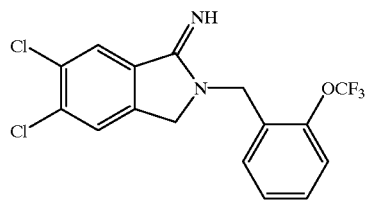

5,6-Dichloro-2-(2-trifluoromethoxy-benzyl)-2,3-dihydro-isoindol-1-ylideneamine Hydrobromide The title compound was prepared utilizing the procedure described in Step E (Example 7) with 2-trifluoromethoxybenzylamine in place of 3-chlorobenzylamine (colorless solid 91%). $^1$H NMR (400 MHz, DMSO-d$_6$) δ9.86 (s, 1 H, NH), 8.54 (s, 1 H, Ar), 8.06 (s, 1 H, Ar), 7.56 (t, J=7.6 Hz, 1 H, Ar), 7.49–7.42 (m, 3 H, Ar), 5.12 (s, 2 H, CH$_2$), 4.76 (s, 2 H, CH$_2$); M/Z (ESI$^+$) 375 ([M+H]$^+$).

EXAMPLE 9

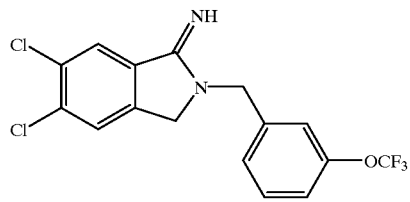

5,6-Dichloro-2-(3-trifluoromethoxy-benzyl)-2,3-dihydro-isoindol-1-ylideneamine Hydrobromide The title compound was prepared utilizing the procedure described in Step E (Example 7) with 3-trifluoromethoxybenzylamine in place of 3-chlorobenzylamine (colorless solid 91%). $^1$H NMR (400 MHz, DMSO-d$_6$) δ9.78 (s, 1 H, NH), 8.52 (s, 1 H, Ar), 8.07 (s, 1 H, Ar), 7.57 (dd, J=8.0, 8.0 Hz, 1 H, Ar), 7.47 (s, 1 H, Ar), 7.41 (d, J=8.0 Hz, 1 H, Ar), 7.39 (d, J=9.3 Hz, $^1$ H, Ar), 5.09 (s, 2 H, CH$_2$), 4.84 (s, 2 H, CH$_2$); M/Z (ESI$^+$) 375 ([M+H]$^+$).

EXAMPLE 10

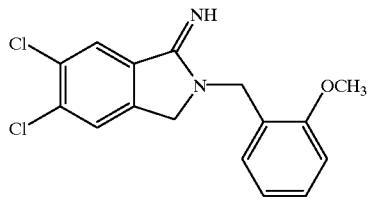

5,6-Dichloro-2-(2-methoxy-benzyl)-2,3-dihydro-isoindol-1-ylideneamine Hydrobromide The title compound was prepared utilizing the procedure described in Step E (Example 7) with 2-methoxybenzylamine in place of 3-chlorobenzylamine (colorless solid 93%). $^1$ H NMR (400 MHz, DMSO-d$_6$) δ9.65 (broad s, 1 H, NH), 8.53 (s, 1 H, Ar), 8.03 (s, 1 H, Ar), 7.40 (dd, J=7.8, 7.8 Hz, 1 H, Ar), 7.30 (d, J=7.3 Hz, 1 H, Ar), 7.10 (d, J=8.2 Hz, 1 H, Ar), 6.99 (dd, J=7.4, 7.4 Hz, 1 H, Ar), 4.95 (s, 2 H, CH$_2$), 4.71 (s, 2 H, CH$_2$), 3.82 (s, 3 H, OCH$_3$); M/Z (ESI$^-$) 321 ([M+H]+$^+$).

EXAMPLE 11

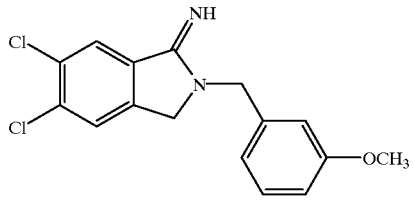

5,6-Dichloro-2-(3-methoxy-benzyl)-2,3-dihydro-isoindol-1-ylideneamine Hydrobromide The title compound was prepared utilizing the procedure described in Step E (Example 7) with 3-methoxybenzylamine in place of 3-chlorobenzylamine, (colorless solid 91%). $^1$H NMR (400 MHz, DMSO-d$_6$) δ9.75 (s, 1 H, NH), 8.52 (s, 1 H, Ar), 8.04 (s, 1 H, Ar), 7.34 (dd, J=7.9, 7.9 Hz, 1 H, Ar), 6.95 (m, 3 H, Ar), 4.99 (s, 2 H, CH$_2$), 4.78 (s, 2 H, CH$_2$), 3.76 (s, 3 H, OCH$_3$); M/Z (ESI$^+$) 321 ([M+H]$^+$).

EXAMPLE 12

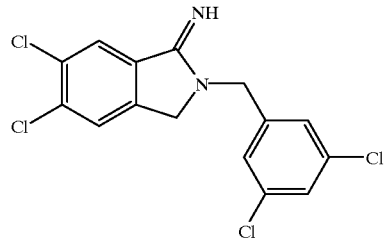

5,6-Dichloro-2-(3,5-dichloro-benzyl)-2,3-dihydro-isoindol-1-ylideneamine Hydrobromide The title compound was prepared utilizing the procedure described in Step E (Example 7) with 3,5-dichlorobenzylamine in place of 3-chlorobenzylamine (colorless solid 91%). $^1$H NMR (400 MHz, DMSO-d$_6$) δ9.72 (s, 1 H, NH), 8.51 (s, 1 H, Ar), 8.07 (s, 1 H, Ar), 7.64 (s, 1 H, Ar), 7.52 (s, 2 H, Ar), 5.03 (s, 2 H, CH$_2$), 4.82 (s, 2 H, CH$_2$); M/Z (ESI$^+$) 359 ([M+H]$^+$).

EXAMPLE 13

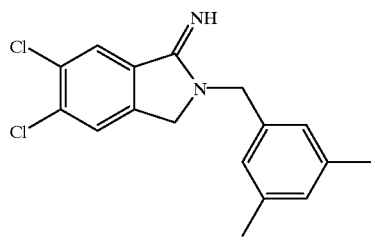

5,6-Dichloro-2-(3,5-dimethyl-benzyl)-2,3-dihydro-isoindol-1-ylideneamine Hydrobromide The title compound was prepared utilizing the procedure described in Step E (Example 7) with 3,5-dimethylbenzylamine in place of 3-chlorobenzylamine (colorless solid>90%). $^1$H NMR (400 MHz, DMSO-d$_6$) δ9.77 (s, 1 H, NH), 8.58 (s, 1 H, Ar), 8.04 (s, 1 H, Ar), 6.99 (d, J=8.1 Hz, 1 H, Ar), 6.98 (s, 1 H, Ar), 4.95 (s, 2 H, CH$_2$), 4.76 (s, 2 H, CH$_2$), 2.27 (s, 6 H, CH$_3$); M/Z (ESI$^+$) 319 ([M+H]$^+$).

EXAMPLE 14

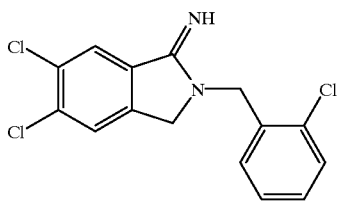

5,6-Dichloro-2-(2-chloro-benzyl)-2,3-dihydro-isoindol-1-ylideneamine Hydrobromide The title compound was prepared utilizing the procedure described in step E (Example 7) with 2-chlorobenzylamine in place of 3-chlorobenzylamine (colorless solid 91%). $^1$H NMR (400 MHz, DMSO-d$_6$) δ9.90 (s, 1H NH), 8.64 (s, 1 H, Ar), 8.07 (s, 1 H, Ar), 7.59 (d, J=7.7 Hz, 1 H, Ar), 7.46–7.38 (m, 3 H, Ar), 5.13 (s, 2 H, CH$_2$), 4.77 (s, 2 H, CH$_2$); M/Z (ESI$^+$) 325 ([M+H]$^+$).

EXAMPLE 15

(Compound 17)

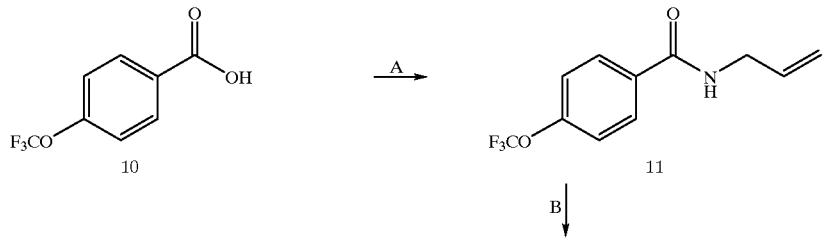

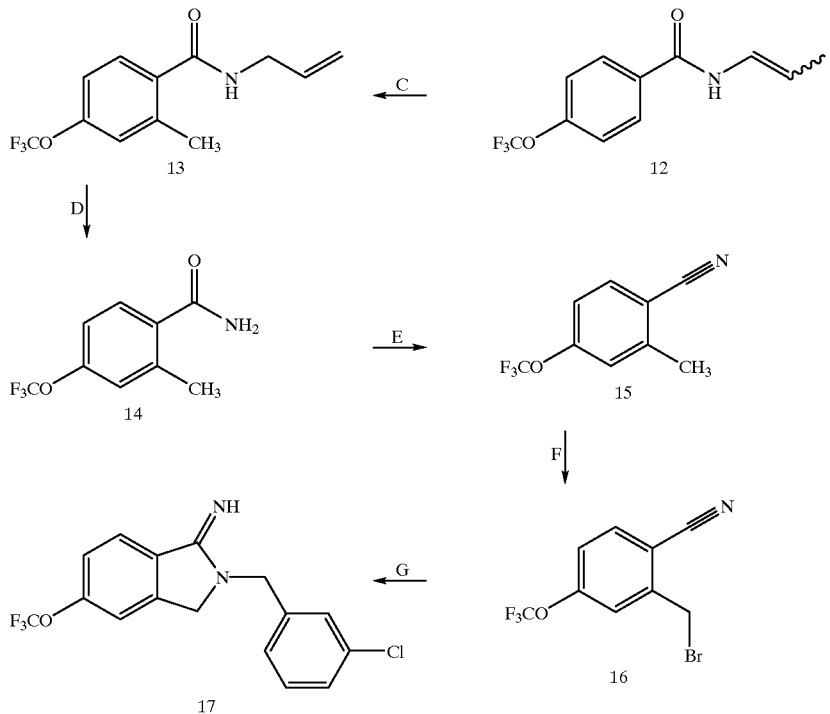

Step A

N-Allyl-4-trifluoromethoxy-benzamide 11

To a solution of 1-hydroxybenzotriazole hydrate (5.4 g, 40 mmol), allyl amine (60 mmol), and 4-(trifluoromethoxy) benzoic acid (8.3 g, 40 mmol) in DMF (110 mL) was added 1-ethyl-3-(3-dimethylaminopropyl)carbodiimide-HCl (11.5 g, 60 mmol) at R.T. After the reaction mixture was stirred for 2.5 hrs, the solution was partitioned between 10% citric acid and ether. The organic layer was washed with sat. aqueous sodium bicarbonate, dried (sodium sulfate), filtered, and concentrated. The residue was purified by silica gel chromatography (20% ether/hexanes) to yield the title compound (colorless solid 96%). $^1$H NMR (400 MHz, CDCl$_3$) δ7.85 (d, J=7.1 Hz, 2 H, Ar), 7.28 (d, J=5.9 Hz, 2 H, Ar), 6.31 (s, 1 H, NH), 5.94 (m, 1 H, CH$_2$CHCH$_2$), 5.25 (dd,J=8.6, 7.1 Hz, 2 H, NHCH$_2$CH), 4.10 (m, 2 H, CHCH$_2$);

Step B

N-Propenyl-4-trifluoromethoxy-benzamide 12

To a solution of diisopropylamine (6.3 mL, 45 mmol) in THF 100 mL at −78° C., was added n-butyllithium (18 mL, 45 mmol of a 2.5M solution in hexanes). After 10 min. a solution (10 mL THF) of N-Allyl-4-trifluoromethoxy-benzamide 11 (5 g, 20 mmol) was added dropwise to the reaction mixture. The resulting dark blue reaction mixture was allowed to warm to 0° C. where it was quenched by addition of aqueous ammonium chloride. Ether was added and the organic layer was separated, dried (sodium sulfate), and concentrated. The residue was purified by silica gel chromatography (20% ether/hexanes) to provide the title compound (colorless solid 85%). $^1$H NMR (400 MHz, CDCl$_3$) δ7.85 (d, J=8.8 Hz, 2 H, Ar), 7.55 (s, 1 H, NH), 7.29 (d, J=9.5 Hz, 2 H, Ar), 6.95 (m, 1 H, NHCHCH), 5.35 & 4.99 (m, 1 H, CHCHCH$_3$), 1.72 (m, 3 H, CH$_3$)

Steps C and D

2-Methyl-4-trifluoromethoxy-benzamide 14

To a solution of N-Propenyl-4-trifluoromethoxy-benzamide 12 (8.0 g, 33 mmol) in THF (100 mL) at −78° C. was added n-butyllithium (29 mL, 72 mmol of a 2.5 M solution in hexanes). The reaction mixture was warmed to −30° C. for 10 min and cooled back to −78° C. A solution of MeI (2.24 mL, 33 mmol) in THF (5 mL) was slowly added to the reaction mixture. The cooling bath was removed and once the reaction temperature warmed to 0° C., 3 N HCl (10 mL) was added and the resulting two phase mixture heated to 60° C. for 1 h. Upon completion of reaction, the solution was neutralized with aqueous sodium bicarbonate and extracted with ether. The combined organic layers were dried (sodium sulfate) and concentrated. The residue was purified by ether/hexane triturated to provide the title compound (colorless solid 75%). $^1$H NMR (400 MHz, CDCl$_3$) δ7.50 (d, J=8.4 Hz, 1 H, Ar), 7.09 (m, 2 H, Ar), 5.74 (broad s, 2 H, NH$_2$), 2.52 (s, 3 H, CH$_3$)

Step E

2-Methyl-4-trifluoromethoxy-benzonitrile 15

2-Methyl-4-trifluoromethoxy-benzamide 14 (2.0 g, 9.1 mmol) was taken up in phosphorus oxychloride (15 mL) and heated to 85° C. for 2 hrs. The excess phosphorus oxychloride was removed under reduced pressure and the resulting residue partitioned between sat. aqueous sodium bicarbonate and ether. The organic layer was dried (sodium sulfate) and concentrated. The residue was passed through silica gel using 25% ether/hexanes to remove trace impurities and yielded a colorless solid (90%). $^1$H NMR (400 MHz,CDCl$_3$) δ7.65 (d, J=8.4 Hz. 1 H, Ar), 7.17 (s, 1 H, Ar), 7.13 (d, J=8.4 Hz, 1 H, Ar), 2.6 (s, 3 H, CH$_3$).

Step F

2-Bromomethyl-4-trifluoromethoxy-benzonitrile 16

To a solution of 2-methyl-4-trifluoromethoxy-benzonitrile 15 (1.3 g, 6.5 mmol) in carbon tetrachloride (25 mL) was added N-bromosuccinimide (1.7 g, 9.7 mmol) and 2,2'-azobisisobutyronitrile (cat.). The reaction mixture was refluxed 6 hrs, filtered, concentrated, and partitioned between ether and water. The ether layer was dried, concentrated, and purified by silica gel chromatography (10% ether/hexanes) to yield a clear oil (70%). $^1$H NMR (400 MHz,CDCl$_3$) δ7.73 (d, J=8.4 Hz, 1 H, Ar), 7.41 (s, 1 H, Ar), 7.27 (d, J=8.4 Hz, 19 H, Ar), 4.61 (s, 2 H, CH$_2$).

Step G 2-(3-Chloro-benzyl)-5-trifluoromethoxy-2,3-dihydro-isoindol-1-ylideneamine Hydrobromide 17

To a solution of 3-chlorobenzylamine (62 mg, 0.442 mmol) in ethanol (500 μL) at 80° C. was added 2-bromomethyl-4-trifluoromethoxy-benzonitrile 16 (95 mg, 0.34 mmol) as a solution in ethanol (100 μL). After 30 min at 80° C., the ethanol was removed under reduced pressure, and the resulting residue was triturated with ether/ethanol to yield the title compound (colorless solid 90%). $^1$H NMR (400 MHz, CD$_3$OD) δ8.48 (d, J=8.0 Hz, 1 H, Ar), 7.78 (s, 1 H, Ar), 7.71 (d, J=8.8 Hz, 1 H, Ar), 7.56 (s, 1 H, Ar), 7.45 (m, 2 H, Ar), 7.38 (m, 1 H, Ar), 5.12 (s, 2 H, CH$_2$), 4.84 (s, 2 H, CH$_2$); M/Z (ESI$^+$) 341 ([M+H]$^+$).

EXAMPLE 16

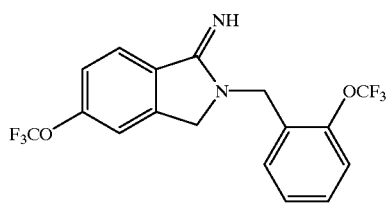

5-Trifluoromethoxy-2-(2-trifluoromethoxy-benzyl)-2,3-dihydro-isoindol-1-ylideneamine Hydrobromide The title compound was prepared utilizing the procedure described in Step G (Example 15) with 2-trifluoromethoxybenzylamine in place of 3-chlorobenzylamine (colorless solid 91%). $^1$H NMR (400 MHz, CD$_3$OD) δ8.24 (d, J=8.8 Hz, 1 H, Ar), 7.67 (s, 1 H, Ar), 7.59 (m, 2 H, Ar), 7.48 (m, 3 H, Ar), 5.15 (s, 2 H, CH$_2$), 4.78 (s, 2 H, CH$_2$); M/Z (ESI$^+$) 391 ([M+H]$^+$).

EXAMPLE 17

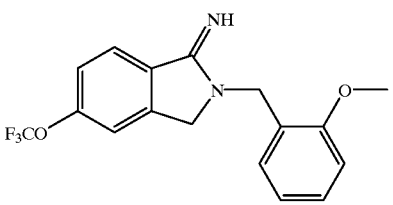

2-(2-Methoxy-benzyl)-5-trifluoromethoxy-2,3-dihydro-isoindol-1-ylideneamine Hydrobromide The title compound was prepared utilizing the procedure described in Step G (Example 15) with 2-methoxybenzylamine in place of 3-chlorobenzylamine (colorless solid 89%). $^1$H NMR (400 MHz, CD$_3$OD) δ8.19 (d, J=8.8 Hz, 1 H, Ar), 7.63 (s, 1 H, Ar), 7.58 (d, J=9.2 Hz, 1 H, Ar), 7.43 (m, 1 H, Ar), 7.36 (dd, J=1.2, 7.2 Hz, 1 H, Ar), 7.09 (d, J=8.4 Hz, 1H, Ar), 7.03 (m, 1 H, Ar), 4.98 (s, 2H, CH$_2$), 4.72 (s, 2 H, CH$_2$), 3.87 (s, 3 H, CH$_3$); M/Z (ESI$^+$) 337 ([M+H]$^+$).

EXAMPLE 18

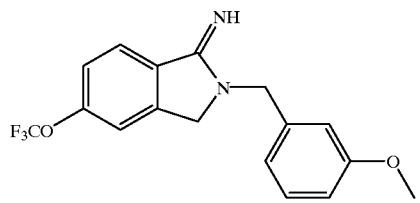

2-(3-Methoxy-benzyl)-5-trifluoromethoxy-2,3-dihydro-isoindol-1-ylideneamine Hydrobromide The title compound was prepared utilizing the procedure described in Step G (Example 15) with 3-methoxybenzylamine in place of 3-chlorobenzylamine, (colorless solid 89%). $^1$H NMR (400 MHz, CD$_3$OD) δ8.24 (d, J=8.4 Hz, 1 H, Ar), 7.66 (s, 1 H, Ar), 7.59 (d, J=8.8 Hz, 1 H, Ar), 7.36 (m, 1 H, Ar), 6.97 (m, 3 H, Ar), 5.01 (s, 2 H, CH$_2$), 4.84 (s, 2 H, CH$_2$), 3.81 (s, 3 H, CH$_3$); M/Z (ESI$^+$) 337 ([M+H]$^+$).

EXAMPLE 19

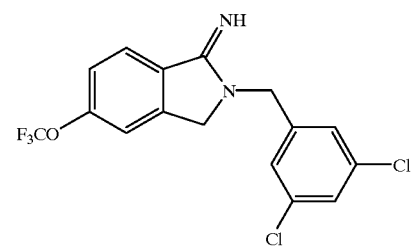

2-(3,5-Dichloro-benzyl)-5-trifluoromethoxy-2,3-dihydro-isoindol-1-ylideneamine Hydrobromide The title compound was prepared utilizing the procedure described in Step G (Example 15) with 3,5-dichlorobenzylamine in place of 3-chlorobenzylamine (colorless solid 87%). $^1$H NMR (400 MHz, CD$_3$OD) δ8.24 (d, J=8.4 Hz, 1 H, Ar), 7.68 (s, 1 H, Ar), 7.60 (d, J=8.8 Hz, 1 H, Ar), 7.5 (m, 1 H, Ar), 7.39 (m, 2 H, Ar), 5.04 (s, 2 H, CH$_2$), 4.88 (s, 2 H, CH$_2$). M/Z (ESI$^+$) 375 ([M+H]$^+$)

EXAMPLE 20

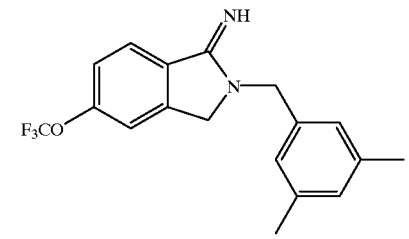

2-(3,5-Dimethyl-benzyl)-5-trifluoromethoxy-2,3-dihydro-isoindol-1-ylideneamine Hydrobromide The title compound was prepared utilizing the procedure described in Step G (Scheme 3) with 3,5- dimethylbenzylamine in place of 3-chlorobenzylamine (colorless solid 86%). $^1$H NMR (400 MHz, CD$_3$OD) δ8.22 (d, J=8.8 Hz, 1 H, Ar), 7.65 (s, 1 H, Ar), 7.58 (d, J=8.4 Hz, 1 H, Ar), 7.04 (s, 1 H, Ar), 6.99 (s, 2 H, Ar), 4.95 (s, 2 H, CH$_2$), 4.80 (s, 2 H, CH$_2$), 2.31 (s, 6 H, CH$_3$); M/Z (ESI$^+$) 335 ([M+H]$^+$).

EXAMPLE 21
(Compound 12)

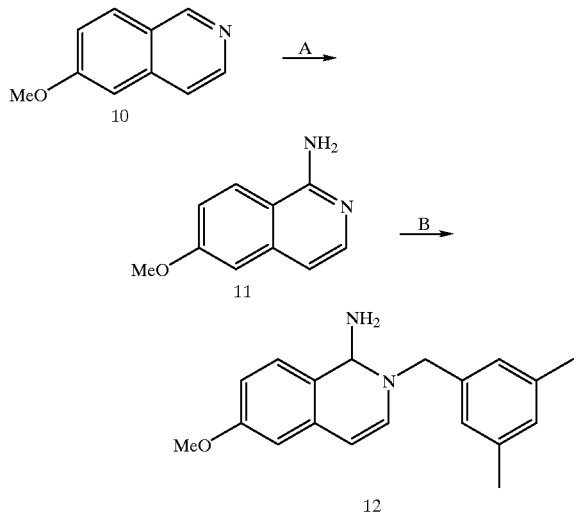

Experimental
Step A

Compound 10 (J.O.C. '83 p3344) (1 g, 6.2 mmol) was combined with sodium amide (excess, suspension in toluene) and refluxed in toluene for 4 hrs. The reaction mixture was carefully added to a rapidly stirring solution of aqueous ammonium chloride at 0° C. The solution was extracted with methylene chloride, dried (sodium sulfate), filtered, concentrated, and purified by silica gel chromatography (ethyl acetate/hexanes) to yield 11 (60% ).

Step B

Compound 11 (100 mg, 0.57 mmol) was combined with 3,5-dimethylbenzyl bromide (0.57 mmol) and heated in toluene to 100° C. for 2 hours. The resulting mixture was cooled and washed with aqueous sodium bicarbonate and extracted with methylene chloride. The organic extract was dried (sodium sulfate), filtered, and purified by silica gel chromatography (methylene chloride, methanol) to yield 12 (example 21) (65%). $^1$H NMR (400 MHz, CDCl$_3$) δ8.57 (d, J=8.0 Hz, 1 H, Ar), 7.13 (dd, J=2.8, 9.2 Hz, 1 H, Ar), 6.99 (d, J=7.2 Hz, 1 H, Ar), 6.89 (s, 3 H, Ar), 6.85 (d, J=2.8 Hz, 1 H, Ar), 6.42 (d, J=7.2 Hz, 1 H, Ar), 5.36 (s, 2 H, CH$_2$), 3.90 (s, 3 H, CH$_3$O), 2.24 (s, 6 H, CH$_3$); M/Z (ESI$^+$) 293 ([M+H]$^+$).

The utility of the compounds of the invention can be demonstrated by one or more of the following biological assays:

[3H] Ifenprodil Binding to Recombinant Human NR1a/NR2B Receptors

Ifenprodil is an NMDA receptor antagonist which acts through a distinct modulatory site to those of glutamate, glycine and MK-801 and is selective for NR2B-containing receptors (Grimwood et al., 1996a). [3H] Ifenprodil binding to cell membranes expressing recombinant human NR1a/NR2B receptors was essentially as described by Grimwood et al. (1996b). In brief, 100 ug of cell homogenate was incubated with [3H] Ifenprodil (NEN) and 50 mM Tris acetate buffer (pH 7.0) on ice. Non-specific binding is determined by addition of 10 micromolar CP-101,606 to a series of wells. After 2 hours, free radioactivity was separated from bound by filtration through Whatman GF/B filters using a cell harvester. Filters were soaked overnight in scintillation fluid and levels of radioactivity determined using a scintillation counter. Inhibition curves were analysed assuming a one-site model.

Functional Ca++ Antagonism Assay-FLIPR

Human NR1a/2B receptor transfected cells are plated in a 96-well format and grown for one day in normal growth media (Dulbeccos MEM with Na pyruvate). NR1a/2B-expression in these cells is induced by the addition of dexamethasone in the presence of ketamine for 16–24 hours. After receptor induction cells are washed with assay buffer (Hanks balanced salt solution (HBSS-Mg free) containing 20 mM HEPES, 0.1% BSA, 2 mM CaCl$_2$ and 250 uM probenecid). Each 96 well cell plate is loaded with the Ca$^{++}$ sensitive dye Fluo-3 (Molecular Probes, Inc.) in assay buffer. The cells are then washed with assay buffer leaving them in 100 ul buffer. Test compounds in solution are pipetted by FLIPR (Fluorometric Imaging Plate Reader, Molecular Dynamics) for 2 min pretreatment. During this time the fluorescence intensity is recorded (excitation at 488 nm and emission at 530 nm). The glutamate/glycine 50 ul agonist solution (final concentration 1 uM/1 uM) is then added by FLIPR into each well already containing 150 ul of buffer (containing the test compound or vehicle) and the fluorescence is continuously monitored for 10 min. Fluorescence values in the presence of an antagonist are compared to those for the agonist alone.

Carrageenan-induced Mechanical Hyperalgesia in Rats

The ability of the agents to reverse carrageenan induced hyperalgesia was determined using the method described by Boyce et al. (1994). Essentially, the animal's hind paw was positioned over a convex surface and gradually increasing pressure applied to the dorsal surface until the animals vocalized or withdrew. The mechanical thresholds were determnined for both hind paws to provide a baseline for comparison following injection of carrageenan into one paw. Rats received an intraplantar injection of carrageenan or saline into one hind paw and mechanical thresholds of both hind paws were re-determined 3 h later. Carrageenan-induced hyperalgesia was defined as the difference in threshold between rats that received intraplantar injection of saline or carrageenan. Test compounds were administered 2 hours after carrageenan and hyperalgesia expressed as a percentage inhibition induced by carrageenan.

The Examples above all have been shown to demonstrate a 50% inhibition of Ifenprodil binding at a concentration of less than 5 μM.

What is claimed is:

1. A compound of Formula I

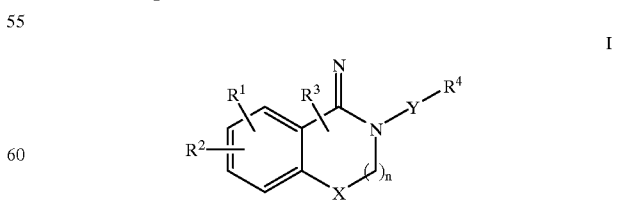

or a pharmaceutically acceptable salt thereof wherein:
R$^1$ is selected from the group consisting of
(a) hydrogen,
(b) C$_{1-6}$alkyl, (c) Br, Cl, F or I, and
(d) $C_{1-6}$alkoxy, optionally mono or di- or tri-substituted with a halo independently selected from Br, Cl, F and I, $R^2$ is selected from the group consisting of
(a) $C_{1-6}$alkyl,
(b) Br, Cl, F or I, and
(c) $C_{1-6}$alkoxy, optionally mono or di- or tri-substituted with a
halo independently selected from Br, Cl, F and I;

$R^3$ is hydrogen or $C_{1-6}$alkyl;

$R^4$ is selected from the group consisting of
(a) hydrogen,
(b) phenyl or naphthyl, optionally mono, di- or tri-substituted with substituents independently selected from
(1) $C_{1-6}$alkyl,
(2) Br, Cl, F or I,
(3) $C_{1-6}$alkoxy, optionally mono or di- or tri-substituted with a halo independently selected from Br, Cl, F and I;

n is 0, and X is $CH_2$, Y is $C_{1-6}$alkylene.

2. A compound according to claim 1 wherein $R^1$ is selected from the group consisting of
(a) hydrogen,
(b) Br, Cl, F or I, and
(c) $C_{1-3}$alkoxy, optionally mono or di- or tri-substituted with a halo independently selected from Br, Cl, F and I.

3. A compound according to claim 2 wherein $R^1$ is selected from the group consisting of
(a) hydrogen,
(b) Br, Cl, F or I, and
(c) $C_{1-3}$alkoxy, optionally mono or di- or tri-substituted with a halo independently selected from Br, Cl F and I; and $R^2$ is selected from the group consisting of
(a) Br, Cl, F or I, and
(b) $C_{1-3}$alkoxy, optionally mono or di- or tri-substituted with a halo independently selected from Br, Cl, F and I.

4. A compound according to claim 1 wherein $R^3$ is selected from the group consisting of
(a) hydrogen, and
(b) $C_{1-3}$alkyl.

5. A compound according to claim 1 wherein $R^4$ is selected from the group consisting of
(a) hydrogen,
(b) phenyl or naphthyl, optionally mono, di- or tri-substituted with substituents independently selected from
(1) $C_{1-3}$alkyl,
(2) Br, Cl, F or I,
(3) $C_{1-3}$alkoxy, optionally mono or di- or tri-substituted with a halo independently selected from Br, Cl, F and I.

6. A compound according to claim 1 wherein

Y is methylene or ethylene.

7. A compound of Formula II

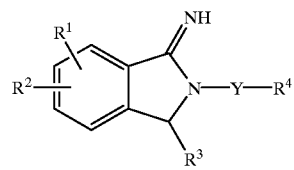

or a pharmaceutically acceptable salt thereof wherein:

$R^1$ is selected from the group consisting of
(a) hydrogen,
(b) $C_{1-6}$alkyl,
(c) Br, Cl, F or I,
(d) $C_{1-6}$alkoxy, optionally mono or di- or tri-substituted with a halo independently selected from Br, Cl, F and I, $R^2$ is selected from the group consisting of
(a) $C_{1-6}$alkyl,
(b) Br, Cl, F or I,
(c) $C_{1-6}$alkoxy, optionally mono or di- or tri-substituted with a halo independently selected from Br, Cl, F and I, or $R^1$ and $R^2$ may be joined so that together with the atoms to which they are attached there is formed a ring selected from the group consisting of:
(a) cyclopentane,
(b) cyclohexane,
(c) furan,
(d) phenyl, and
(e) a five (5) or six (6) membered saturated or unsaturated heterocycle containing one, two or three heteroatoms selected from the group consisting of S, O and N,
said ring optionally mono, di, tri or tetra-substituted with a halo independently selected from
Br, Cl, F and I, $R^3$ is hydrogen or $C_{1-6}$alkyl;

$R^4$ is selected from the group consisting of
(a) hydrogen,
(b) phenyl or naphthyl, optionally mono, di- or tri-substituted with substituents independently selected from
(1) $C_{1-6}$alkyl,
(2) Br, Cl, F or I,
(3) $C_{1-6}$alkoxy, optionally mono or di- or tri-substituted with a halo independently selected from Br, Cl, F and I; and Y is $C_{1-6}$alkylene.

8. A compound according to claim 7 wherein $R^1$ is selected from the group consisting of
(a) hydrogen,
(b) Br, Cl, F or I, and
(c) $C_{1-3}$alkoxy, optionally mono or di- or tri-substituted with a halo independently selected from Br, Cl, F and I.

9. A compound according to claim 7 wherein $R^1$ is selected from the group consisting of
(a) hydrogen,
(b) Br, Cl, F or I, and
(c) $C_{1-3}$alkoxy, optionally mono or di- or tri-substituted with a halo independently selected from Br, Cl F and I; and $R^2$ is selected from the group consisting of (a) Br, Cl, F or I, and
(b) $C_{1-3}$alkoxy, optionally mono or di- or tri-substituted with a halo independently selected from Br, Cl, F and I.

10. A compound according to claim 7 wherein
$R^3$ is selected from the group consisting of
(a) hydrogen, and
(b) $C_{1-3}$alkyl.

11. A compound according to claim 7 wherein
$R^4$ is selected from the group consisting of
(a) hydrogen,
(b) phenyl or naphthyl, optionally mono, di- or tri-substituted with substituents independently selected from
  (1) $C_{1-3}$alkyl,
  (2) Br, Cl, F or I,
  (3) $C_{1-3}$alkoxy, optionally mono or di- or tri-substituted with a halo independently selected from Br, Cl, F and I.

12. A compound according to claim 7 wherein
Y is methylene or ethylene.

13. A compound according to claim 12 wherein
$R^1$ is selected from the group consisting of
(a) hydrogen,
(b) Br, Cl F or I, and
(c) $C_{1-3}$alkoxy, optionally mono or di- or tri-substituted with a halo independently selected from Br, Cl, F and I; and
$R^2$ is selected from the group consisting of
(a) Br, Cl, F or I, and
(b) $C_{1-3}$alkoxy, optionally mono or di- or tri-substituted with a halo independently selected from Br, Cl, F and I;
$R^3$ is selected from the group consisting of
(a) hydrogen, and
(b) $C_{1-3}$alkyl;
$R^4$ is selected from the group consisting of phenyl or naphthyl, optionally mono, di- or tri-substituted with substituents independently selected from
(a) C1–3 alkyl,
(b) Br, Cl, F or I,
(c) $C_{1-3}$alkoxy, optionally mono or di- or tri-substituted with a halo independently selected from Br, Cl, F and I; and
Y is methylene or ethylene.

14. A compound according to claim 13 wherein
$R^1$ is selected from the group consisting of
(a) hydrogen,
(b) Br, Cl F or I, and
(c) methoxy, optionally mono or di- or tri-substituted with a halo independently selected from Br, Cl, F and I; and
$R^2$ is selected from the group consisting of
(a) Br, Cl, F or I, and
(b) methoxy, optionally mono or di- or tri-substituted with a halo independently selected from Br, Cl F and I, $R^3$ is selected from the group consisting of
(a) hydrogen, and
(b) methyl;
$R^4$ is selected from the group consisting of phenyl, optionally mono, di- or tri-substituted with substituents independently selected from
(a) methyl,
(b) Br, Cl, F or I,
(c) methoxy; and
Y is methylene or ethylene.

15. A compound according to claim 1 selected from the group consisting of (a) 5-Choro-2-(2-trifluoromethoxy-benzyl)-2,3-dihydro-isoindol-1-ylideneamine Hydrobromide,
(b) 5-Chloro-2-(3,5-dimethyl-benzyl)-2,3-dihydro-isoindol-1-ylidenaeamine Hydrobromide,
(c) 5-Chloro-2-(3,5-dichloro-benzyl)-2,3-dihydro-isoindol-1-ylideneamine Hydrobromide,
(d) 5-Chloro-2-(3-methoxy-benzyl)-2,3-dihydro-isoindol-1-ylideneamine,
(e) 5,6-Dichloro-2-(3-chloro-benyl)-2,3-dihydro-isoindol-1-ylideneamine Hydrobromide,
(f) 5,6-Dichloro-2-)2-trifluoromethoxy-benzyl)-2,3-dihydro-isoindol-1-ylideneamine Hydrobromide,
(g) 5,6-Dicholoro-2-(2-methoxy-benzyl)-2,3-dihydro-isoindol-1-ylideneamine Hydrobromide,
(h) 5,6-Dichloro-2-(3-methoxy-benzyl)-2,3-dihydro-isoindol-1-ylideneamine Hydrobromide,
(i) 6-Dichloro-2-(3-dichloro-benzyl)-2,3-dihydro-isoindol-1-ylideneamine Hydrobromide,
(j) 5,6-Dichloro-2-(3-dimethyl-benzyl)-2,3-dihydro-isoindol-1-ylideneamine Hydrobromide,
(k) 5,6-Dichloro-2-(3-chloro-benzyl)-2,3-dihydro-isoindol-1-ylideneamine Hydrobromide,
(l) 2-(3-Chloro-benzyl)-5-trifluoromethoxy-2,3-dihydro-isoindol-1-ylideneamine Hydrobromide,
(m) 5-Trifluoromethoxy-2-(2-trifluoromethoxy-benzyl)-2,3-dihydro-isoindol-1-ylideneamine Hydrobromide,
(n) 2-(2-Methozy-benzyl)-5-trifluoromethoxy-2,3-dihydro-isoindol-1-ylideneamine Hydrobromide,
(o) 2-(3-Methozy-benzyl)-5-trifluoromethoxy-2,3-dihydro-isoindol-1-ylideneamine Hydrobromide,
(p) 2-(3,5-Dichloro-benzyl)-5-trifluoromethoxy-2,3-dihydro-isoindol-1-ylideneamine Hydrobromide, and
(o) 2-(3,5-Dimethyl-benzyl)-5-trifluoromethoxy-2,3-dihydro-isoindol-1-ylideneamine Hydrobromide.

16. A pharmaceutical composition comprising a therapeutically effective amount of compound according to claim 1 and a pharmaceutically acceptable carrier.

17. A method of treating a NMDA mediated Disease comprising administration to a patient in need of such treatment a non-toxic amount of a compound of claim 1 effective to block the NMDA NR2B receptor sub-unit.

* * * * *